United States Patent [19]

Shimizu

[11] 4,276,537

[45] Jun. 30, 1981

[54] MOISTURE-RESPONSIVE RESISTOR ELEMENT

[75] Inventor: Hiroshi Shimizu, Mooka, Japan

[73] Assignee: Sanyo Silicon Electronics Co., Ltd., Tochigi, Japan

[21] Appl. No.: 104,711

[22] Filed: Dec. 18, 1979

[30] Foreign Application Priority Data

Dec. 20, 1978 [JP] Japan ............................ 53-159423
Dec. 21, 1978 [JP] Japan ............................ 53-159424

[51] Int. Cl.$^3$ ............................................. H01L 7/00
[52] U.S. Cl. ..................................... 338/35; 252/518

[58] Field of Search ................... 338/35, 34; 252/518; 200/61.06; 73/27 R; 23/232 E; 422/98

[56] References Cited

U.S. PATENT DOCUMENTS 4,086,556  4/1978  Nitta et al. ..................... 252/518 X Primary Examiner—C. L. Albritton
Attorney, Agent, or Firm—Fleit & Jacobson

[57] ABSTRACT

A moisture-responsive resistor element comprising, as a moisture-responsive resistance material, metastannic acid alone or in combination with tin dioxide.

5 Claims, 8 Drawing Figures

MOISTURE-RESPONSIVE RESISTOR ELEMENT

BACKGROUND OF THE INVENTION

The present invention relates to a so-called moisture-responsive resistor element in which the electric resistance is changed depending on the humidity. More particularly, the present invention relates to a moisture-responsive resistor element of the direct current driving type for measuring the relative humidity.

A moisture-responsive resistor element is utilized for not only a hygrometer but also an apparatus in which electric control is automatically performed according to the change of the humidity, for example, a drier or dehumidifier.

As a conventional moisture-responsive resistor element, there is known an element formed by mixing a metal oxide with a catalyst or mixing metal oxides together, fixing the mixture to a substrate or coating a paste of the mixture on a substrate, and sintering the mixture. However, the resistivity of the conventional moisture-responsive resistor element of this sinter type is very high, and the thickness and size should be increased so as to reduce the resistivity to a practically applicable level. Furthermore, in the conventional moisture-responsive resistor element, in order to increase the stability and prevent occurrence of polarization, an alternating current of a frequency of about 1 KHz is used for driving of the element. However, in case of alternating current driving, an oscillating circuit or the like should be disposed separately and the circuit structure is complicated. Furthermore, influences of oscillation on other proximity circuits should be taken into account and application of the conventional moisture-responsive resister element of the alternating current driving type involves various difficulties.

SUMMARY OF THE INVENTION

It is a primary object of the present invention to provide a novel moisture-responsive resistor element in which the above-mentioned various defects involved in the conventional moisture-responsive resistor element of the alternating current driving type are overcome and eliminated.

Another object of the present invention is to provide a moisture-responsive resistor element being excellent in reproducibility and having a high response speed.

Still another object of the present invention is to provide a moisture-responsive resistor element in which both the hysteresis and the change of the response characteristic with lapse of the time are reduced.

Still another object of the present invention is to provide a moisture-responsive resistor element having an excellent quality stability.

A further object of the present invention is to provide a moisture-responsive resistor element having a low resistance and a small size.

The applicant made researches on moisture-responsive resistance materials, and as a result, it was found that the direct current resistance value of metastannic acid is changed according to a certain exponential function depending on the relative humidity, this characteristic is not changed even if metastannic acid is exposed to a high-temperature and high-humidity atmosphere in the state where a direct current voltage is applied and that very good characteristics can be obtained by combining metastannic acid with tin dioxide. Based on these findings, the present invention has now been completed.

In accordance with the present invention, there is provided a moisture-responsive resistor element comprising, as a moisture-responsive resistance material, metastannic acid alone or in a combination with tin dioxide.

Metastannic acid may be in the form of a layer or in the bulky form. A structure comprising a layer of metastannic acid formed on an insulating substrate having confronting electrodes of a noble metal or the like is especially preferred. This layer of metastannic acid may be formed according to an optional method. For example, there may be adopted a method in which powder of metastannic acid is formed into a paste and the paste is coated and dried on an insulating substrate to form a layer of metastannic acid thereon. Furthermore, there may be adopted a method in which a thin film of metallic tin is formed on an insulating substrate by vacuum deposition or the like and the metallic tin film is rendered passive by concentrated nitric acid or the like to form a layer of metastannic acid. Still further, there may be adopted a method in which powder of metastannic acid is solidified by a press to form a block of metastannic acid. Moreover, there may be adopted a method in which a mixture of metastannic acid with other insulating material or noble metal is formed into a layer or bulk. In short, any of moisture-responsive resistor elements containing metastannic acid is included in the scope of the present invention.

When metastannic acid is combined with tin dioxide, there are many modes for combining metastannic acid with tin dioxide. For example, it is preferred to adopt a doublelayer structure prepared by applying tin dioxide in the filmy form on an insulating substrate and forming a layer of metastannic acid on the film of tin dioxide. In order to facilitate connection of the element with external lead wires, electrodes of a noble metal such as gold are formed on confronting ends of the so formed moisture-responsive resistance material. In this case, the layer of tin dioxide formed on the insulating substrate can be prepared according to an optional method. For example, there may be adopted a method in which powder of tin dioxide is formed into a paste and the paste is coated and dried on an insulating plate to form a low resistance film of tin dioxide, and a method in which a thin film of metallic tin is formed on an insulating substrate by vacuum deposition or the like and the tin film is converted to a tin dioxide film by an oxidizing treatment. Furthermore, there may be adopted a method in which a layer of metastannic acid is formed on the surface of a tin dioxide resistor in the form of a bulk, a method in which a mixture of powder of tin dioxide and powder of metastannic acid is formed into a paste and the paste is coated and dried on an insulating substrate to form a layer and a method in which a mixture of powder of tin dioxide and powder of metastannic acid is solidified by a press to form a block.

The direct current resistance of metastannic acid per se is changed depending on the change of the humidity in the outer atmosphere. As shown in FIG. 1, the direct current resistance of metastannic acid is changed substantially completely according to a certain exponential function depending on the change of the relative humidity in a relatively high resistance region. However, as will readily be understood from embodiments described hereinafter, this dependency on the relative humidity can also be maintained in a relatively low resistance region, by combining metastannic acid with tin dioxide.

Other objects and features of the present invention will be made apparent from the detailed description of the preferred embodiments thereof, which will be made with reference to the accompanying drawings.

DETAILED DESCRIPTION OF THE INVENTION

Embodiments of the moisture-responsive resistor element according to the present invention will now be described with reference to the accompanying drawings.

Figure 2A:
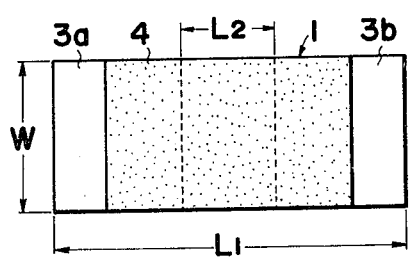
FIG. 2A is a plan view showing the structure of a measurement sample used in one embodiment of the present invention and FIG. 2B is a sectional view showing the measurement sample shown in FIG. 2A.
Figure 2B:
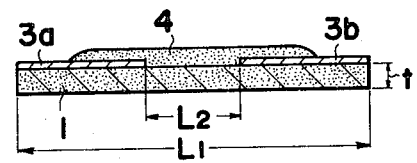

FIGS. 2A and 2B illustrate dimensions of the moisture-responsive resistor element of this embodiment. An alumina ceramic plate 1 as the substrate has a length L1 of 3.0 mm, a width W of 1.2 mm and a thickness of 0.4 mm. Confronting parallel electrodes 3a and 3b of gold are formed on both the sides of one surface of the alumina ceramic plate 1 by vacuum deposition so that the distance L2 between the confronting electrodes 3a and 3b is 0.8 mm. The above dimensions are not critical, and the dimensions of the electrodes and substrate may be appropriately changed depending on the desired value of the electric resistance. Then 2 g of metastannic acid and 40 mg of polyvinyl alcohol (hereinafter referred to as "PVA") as a binder are incorporated into 2 cc of water to form a paste, and the paste is coated on the alumina ceramic substrate 1 having the gold electrodes 3a and 3b so that the paste is partially overlapped on the gold electrodes 3a and 3b. The coated paste is dried to form a layer 4 of metastannic acid. Drying is conducted at 60° C. for about 3 hours.

Figure 1:
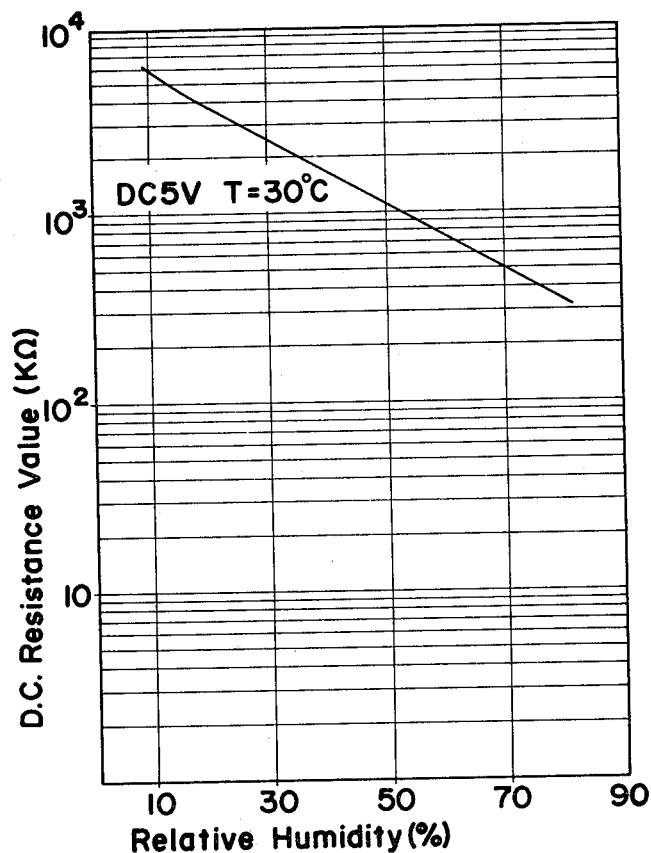
FIG. 1 is a diagram illustrating results of the measurement made by using one embodiment of the moisture-responsive resistor element according to the present invention.

Results of an example of the measurement made by using the so obtained moisture-responsive resistor element are shown in FIG. 1. The measurement is carried out under a direct current voltage of 5 V between terminals and at a temperature of 30° C. As will be apparent from the results shown in FIG. 1, a very prominent characteristic of the so prepared sample is that the direct current resistance value is changed with a good linearity depending on the change of the relative humidity, and from the results shown in FIG. 1, it is confirmed that the sample can be satisfactorily used in the relative humidity range of from 10% to 90%. Incidentally, the moisture-responsive resistor element of this embodiment has a voltage dependency, though this voltage dependency is very small. More specifically, when the direct current voltage applied is changed, the direct current resistance value is changed even if the relative humidity of the atmosphere is not changed. Therefore, when the moisture-responsive resistor element of this embodiment is actually used, it is necessary to take care so that a constant voltage is always applied to the resistor element.

A second embodiment of the present invention will now be described.

Figure 3A:
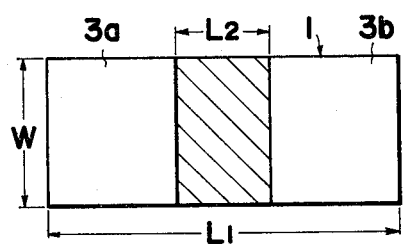
FIG. 3A is a diagram illustrating dimensions of a substrate in one embodiment of the present invention and FIG. 3B is a diagram illustrating the state where a layer of tin dioxide and metastannic acid is formed on the substrate shown in FIG. 3A.

FIG. 3A shows the shape and configuration of the moisture-responsive resistor element of this embodiment. An alumina ceramic plate 1 as the substrate has a length L1 of 3.0 mm, a width W of 1.2 mm and a thickness t of 0.4 mm, and parallel electrodes 3a and 3b of gold are formed on both the sides of one surface of the alumina ceramic plate 1. The distance L2 between the parallel gold electrodes 3a and 3b is 0.8 mm. Accordingly, in FIG. 3A, the hatched area constitutes a sensor region.

Figure 3B:
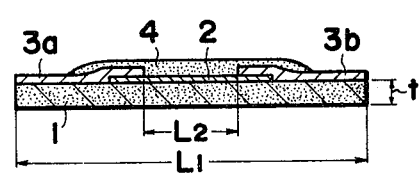

This embodiment is an example of the double-layer structure in which a layer of metastannic acid is formed on a layer of tin dioxide. As shown in FIG. 3B, metallic tin is vacuum-deposited in the central portion of the alumina ceramic plate 1. The thickness of the vacuum-deposited tin film is in the order of about several thousand angstrom units. The metallic tin vacuum-deposited alumina ceramic plate 1 is allowed to stand in air maintained at 700° to 800° C. for about 2 hours to oxidize tin and form a layer of a tin dioxide resistance 2. Then, gold electrodes 3a and 3b are formed on both the sides of the alumina ceramic plate 1 so that the electrodes 3a and 3b are overlapped on both the terminal portions of the tin dioxide resistance 2. The distance L2 between both the electrodes 3a and 3b is adjusted to 0.8 mm. Then, a paste formed by mixing 2 g of metastannic acid and 40 mg of PVA as the binder with 2 cc of water is coated on the tin dioxide resistance 2 so that it is partially overlapped on both the gold electrodes 3a and 3b, and the coated paste is naturally dried to form a layer 4 of metastannic acid. Drying is conducted at 60° C. for about 3 hours. Accordingly, in FIG. 3A, the hatched area having a length L2 of 0.8 mm and a width W of 2 mm constitutes a sensor region.

Figure 5:
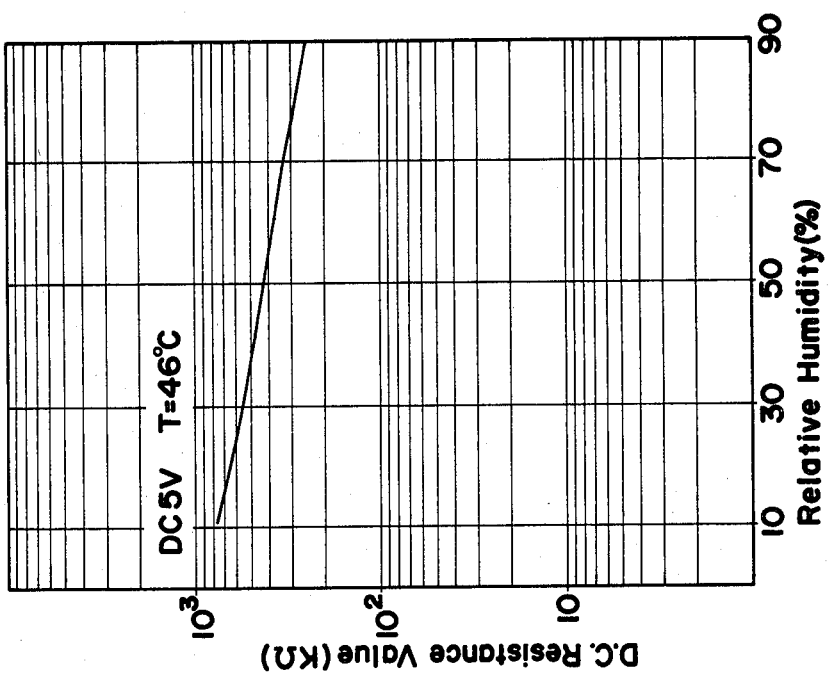
FIG. 5 is a diagram illustrating results of the measurement made by using another embodiment of the moisture-responsive resistor element according to the present invention.

Results of an example of the measurement made by using the so obtained sample are shown in FIG. 5. The measurement was carried out under a direct current voltage of 5 V and at a temperature of 30° C. From the results shown in FIG. 5, it is seen that a very prominent characteristic of this element is that although the size of the element is very small, the direct current resistance is very low and in the range of about 12 to about 40 KΩ. Moreover, the direct current resistance value is changed substantially completely according to a certain exponential function depending on the change of the relative humidity. Accordingly, in the structure of this embodiment, the resistance is changed in a relatively low resistance region, and if the direct current resistance is logarithmically plotted to the relative humidity, a good linearity is manifested. As will be apparent from the foregoing illustration, the size can be reduced and the measurement can be accomplished with very high accuracy, and the resistor element can be used very conveniently.

Figure 4:
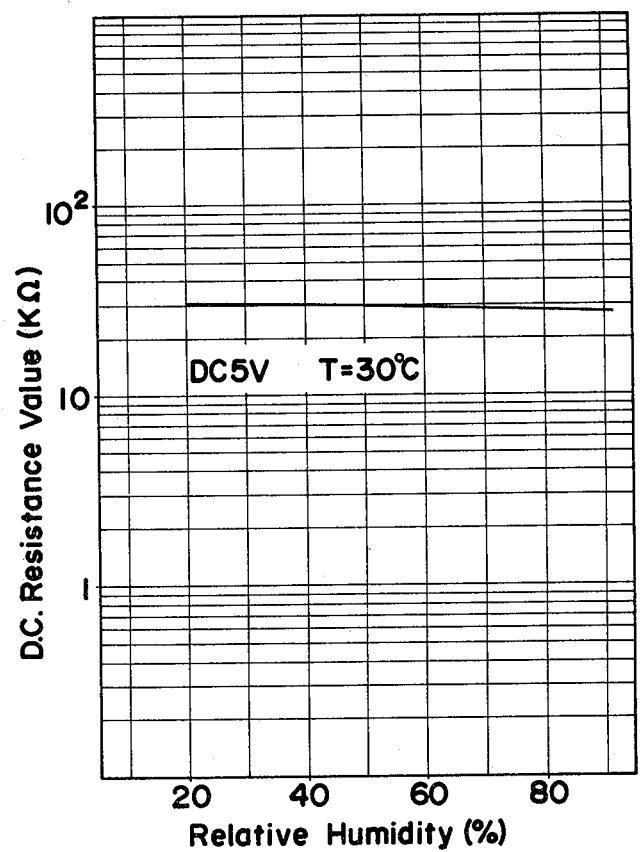
FIG. 4 is a curve illustrating the relative humidity-direct current resistance characteristic of tin dioxide in the form a film.

For reference, as pointed out hereinbefore, the direct current resistance of metastannic acid per se is changed depending on the change of the humidity in the outer atmosphere (see FIG. 1), but the direct current resistance of tin dioxide formed by vacuum deposition is hardly changed even if the relative humidity is changed, as shown in FIG. 4. However, if metastannic acid is placed on such tin dioxide resistance, as shown in FIG. 5, even the resistance value of the tin dioxide resistance is changed according to the change of the relative humidity, the assembly as a whole acts as a moisture-responsive resistor element.

It has been confirmed that the moisture-responsive resistor element of the present embodiment can be satisfactorily used at least within a relative humidity range of from 10% to 90%. The temperature coefficient is about 0.2%/°C. When this element is actually used, it must be noted that the element should be driven by a direct current.

When the moisture-responsive resistor element of the present embodiment is used in a high-temperature and high-humidity atmosphere, it is preferred that the moisture-responsive resistor element prepared according to the above-mentioned method be heat-treated and subjected to high humidity aging (for example, at a temperature of 80° C. and a relative humidity of 95% for 3 hours), whereby the stability of the element can be improved. In this case, the polarity of the voltage applied to the moisture-responsive resistor element during actual use should be the same as the polarity of the voltage applied during the aging treatment. As a result of various experiments, it has been confirmed that the humidity-resistance characteristic hardly depends on the amount of metastannic acid in the resistor element having a double-layer structure as described above. Therefore, if only metastannic acid covers the surface of tin dioxide, the characteristic is hardly changed even when the adherence condition differs.

A third embodiment of the present invention will now be described.

Figure 6:
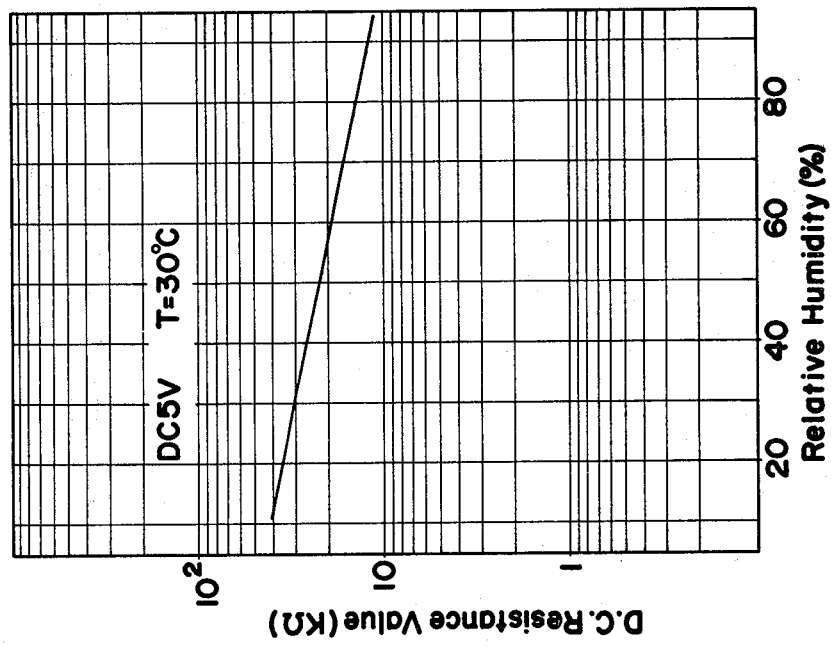
FIG. 6 is a diagram illustrating results of the measurement made by using still another embodiment of the moisture-responsive resistor element according to the present invention.

In this embodiment, a mixture of tin dioxide and metastannic acid is applied onto a substrate. Metastannic acid and tin dioxide are mixed with a binder and water to form a paste, and the paste is coated on the central portion of an alumina ceramic plate 1 having gold electrodes 3a and 3b as shown in FIG. 3A so that the paste is partially overlapped on the gold electrodes 3a and 3b. The applied paste is then naturally dried. In this embodiment, 2 parts by weight of tin dioxide is mixed with 5 parts by weight of metastannic acid. Results of an example of the measurement made by using the so prepared sample are shown in FIG. 6. The measurement is carried out under a direct current voltage of 5 V between terminals and at a temperature of 46° C. From the results shown in FIG. 6, it will readily be understood that the direct current resistance value is changed substantially completely according to a certain exponential function depending on the change of the relative humidity as in the case of the sample of the above-mentioned second embodiment.

When a homogeneous mixture of powders of metastannic acid and tin dioxide is used as in the present embodiment, the ratio of the amount of tin dioxide to the amount of metastannic acid should not be increased beyond a certain limit. If the amount of tin dioxide is too large, tin dioxide appears on the surface of the element and the change of the direct current resistance deviates from the curve of the exponential function, with the result that the use of the element becomes difficult. However, this disadvantage can be eliminated if the concentration of metastannic acid is gradually changed in the thickness direction so that the outer surface is substantially covered with metastannic acid.

In the moisture-responsive resistor element of the present invention having the above-mentioned structure, since metastannic acid alone or in combination with tin dioxide, each being stable and pure, is used, a good reproducibility can be attained. Therefore, elements uniform in characteristics can be manufactured in good yields. Moreover, since the element of the present invention can be driven by a direct current, it can easily be applied to practical use and the circuit structure can be simplified. Moreover, the direct current resistance value is changed substantially completely according to a certain exponential function depending on the change of the relative humidity. Also for this reason, actual application of the resistor element can be remarkably facilitated. Furthermore, the response speed is high, the hysteresis or the change of the response characteristics with lapse of the time can be remarkably reduced, and the stability and reliability can be highly improved. Thus, various effects can be attained according to the present invention.

What is claimed is:

1. A moisture-responsive resistor element of the direct current driving type for measurement of the relative humidity, which comprises metastannic acid as a moisture-responsive resistance material.

2. A moisture-responsive resistor element as set forth in claim 1 wherein the moisture-responsive resistance material comprises tin dioxide in combination with metastannic acid.

3. A moisture-responsive resistor element as set forth in claim 2 wherein the amount of tin dioxide is 2 parts by weight per 5 parts by weight of metastannic acid.

4. A moisture-responsive resistor element as set forth in claim 2 wherein a film of tin dioxide is formed on an insulating substrate and a layer of metastannic acid is formed on said film.

5. A moisture-responsive resistor element as set forth in claim 2 wherein the outer surface of the element is covered with metastannic acid.

* * * * *